(12) United States Patent
Oosterhuis et al.

(10) Patent No.: US 9,988,597 B2
(45) Date of Patent: *Jun. 5, 2018

(54) METHOD AND APPARATUS FOR CULTIVATING CELLS

(75) Inventors: Nicolaas Marius Gerard Oosterhuis, Winterswijk Brinkheurne (NL); Anthonie Tromper, Winterswijk Brinkheurne (NL)

(73) Assignee: Strix Beheer B.V. (NL)

( * ) Notice: Subject to any disclaimer, the term of this patent is extended or adjusted under 35 U.S.C. 154(b) by 587 days.

This patent is subject to a terminal disclaimer.

(21) Appl. No.: 14/370,536

(22) PCT Filed: Jan. 4, 2012

(86) PCT No.: PCT/NL2012/050005
§ 371 (c)(1),
(2), (4) Date: Feb. 16, 2015

(87) PCT Pub. No.: WO2013/103293
PCT Pub. Date: Jul. 11, 2013

(65) Prior Publication Data
US 2015/0166946 A1     Jun. 18, 2015

(51) Int. Cl.
C12M 1/00     (2006.01)
C12M 3/06     (2006.01)
C12M 1/42     (2006.01)
C12M 1/12     (2006.01)
C12M 1/34     (2006.01)

(52) U.S. Cl.
CPC ............ *C12M 23/00* (2013.01); *C12M 23/14* (2013.01); *C12M 25/00* (2013.01); *C12M 27/16* (2013.01); *C12M 35/04* (2013.01); *C12M 41/00* (2013.01)

(58) Field of Classification Search
None
See application file for complete search history.

(56) References Cited

FOREIGN PATENT DOCUMENTS

| | | |
|---|---|---|
| FR | 2519020 A1 | 7/1983 |
| WO | 2008153401 A1 | 12/2008 |
| WO | 2011003615 A2 | 1/2011 |

OTHER PUBLICATIONS

FR 2529020 English Translation (1983).*
International Search Report issued from corresponding PCT/NL2012/050005, dated Aug. 21, 2012.

* cited by examiner

*Primary Examiner* — Suzanne M Noakes
*Assistant Examiner* — Stephen M Chong
(74) *Attorney, Agent, or Firm* — Banner & Witcoff, Ltd.

(57) ABSTRACT

In a method for cultivating cells, there is provided a container (4) comprising an at least partly flexible container wall structure (41). The container is at least resting on a support structure (2). Into the container's interior space (42) there is introduced a gas, a liquid medium (5) and a cell culture. At least part of said support structure together with the container thus resting thereon are being moved, thereby inducing motion to the liquid medium in the container. An upwardly facing outer surface structure of said support structure comprises an elongate downwardly recessed portion (24, 25, 26) which causes a gutter (7) in the container's bottom wall structure (43).

4 Claims, 4 Drawing Sheets

METHOD AND APPARATUS FOR CULTIVATING CELLS

RELATED APPLICATION DATA

This application is a National Stage Application under 35 U.S.C. 371 of co-pending PCT application PCT/NL2012/050005 designating the United States and filed Jan. 4, 2012 which is hereby incorporated by reference in its entirety.

The invention relates to the field of biotechnology and industrial scale cell culturing. In particular, it relates to a method and an apparatus for cultivating cells. More in particular, the invention relates to a method according to the pre-characterizing portion of appended independent claim 1, as well as to an apparatus according to the pre-characterizing portion of appended independent claim 8.

Such a method and such an apparatus are for example known from U.S. Pat. No. 6,190,913B1. This known technique employs a pre-sterilized flexible plastic bag in which cells are cultivated. The bag is partially filled with growth media and the remainder of the bag is continuously purged with air or other oxygen-rich gas. The bag is secured to a rocking platform that is rocked to and fro about a horizontal axis. The rocking motion promotes wave formation in the bag which provides liquid mixing and enhances oxygen transfer from the headspace gas to the liquid phase where it is essential for cell growth and metabolism.

Usually, cell cultivating is started by introducing an inoculation cell culture in a relatively small container comprising a relatively small volume of liquid growth medium, like 200 milliliter, such that the cell density is within an optimal range for cell replication. Subsequently, the starting culture is expanded by a step-wise transfer to containers of increasing size, for example up to a cell culture volume of 20 liters or even more, ensuring that the cell density is maintained within the required range.

So usually, and for example when applying the abovementioned technique known from U.S. Pat. No. 6,190,913B1, cell culture expansion from a small inoculation culture to a large 'working-culture' is not performed in the same container. This especially holds for very small inoculation cultures with orders of magnitude of less than 200, 150 or 100 milliliter of liquid growth medium. The reason is that the dimensions of a container that can accommodate the volume of a working-culture, e.g. a 20 liter working-culture, are obviously unsuitable to accommodate such initial very small starting culture. When a very small starting culture would be cultivated in a large working-culture container (like having a total volume of 30 liter or more), the liquid layer would be very thin (like less than 4, 3 or 2 millimeter). Such a very thin liquid layer results into poor mixing, since the liquid is spread out very widely over the bottom of the container. Such a very thin liquid layer also results into high exposure of the cells to damaging shear stress levels.

Each step of the step-wise transfer of a cell culture to a larger container is a critical procedure as it carries the risk of introducing an infection or a contamination into the culture. Furthermore, it is very labour-intensive.

It is an object of the invention to provide a solution according to which, starting off with a very small starting culture in a container, the culture expansion can be performed in that same container, with good liquid mixing and only limited exposure of the cells to damaging shear stress levels also during the cultivating of the very small starting culture in the container.

According to the present invention, this object is achieved by providing a method according to appended independent claim 1. The invention may also be embodied in an apparatus according to appended independent claim 8.

Hence, according to the invention, a gutter in the container bottom wall structure is formed, which gutter forming is automatical thanks to the elongate downwardly recessed portion of the upwardly facing outer surface structure of the support structure and thanks to the flexibility of the container. In operation, the moving liquid medium will continuously be driven into the gutter, which takes place automatically under the influence of gravity. The result is that, when a very small starting culture is being cultivated in a large 'working-culture' container, the occurrence of too small liquid levels (i.e. too thin liquid layers) is effectively prevented thanks to the gutter. This enables good liquid mixing and only limited exposure of the cells to damaging shear stress levels. And when the culture is expanding more and more in the large container, there will be an increasing surface area of the container bottom wall structure that will be covered by an increasing amount of liquid, thus allowing the culture expansion to be performed in the same container without influencing the culture behaviour.

It is noted that WO2008/153401A1 more or less provides an alternative solution for the abovementioned object of the invention. In FIGS. 7, 8 and 9 of WO2008/153401A1 there is shown a bag 1 having two hollow seams 15 in its bottom wall, each hollow seam 15 containing a rod 14 therein. Around each rod 14 there can be tightly fitted a separate pressing device 21 (see FIG. 6 of WO2008/153401A1) having an omega-shaped plastic profile 22. By means of said seams 15, said rods 14 and said pressing devices 21, said bag 1 can selectively be brought in either a first or a second condition shown in FIGS. 8 and 9 of WO2008/153401A1, respectively. In the first condition the effective volume of said bag is smaller than in the second condition. Hence, said bag 1 can be used to reduce the number of steps in the step-wise transferring of cell cultures to larger containers.

However, the alternative solution provided by WO2008/153401A1 has drawbacks. One drawback is that said seams 15 have to be prepositioned at manufacture of the bag, which limits the operational flexibility. Another drawback is that, when said bag 1 is inflated with air, as is usually done during cultivation, the seams tend to come loose and undesirable leaking of liquid to other compartments is the result. A further drawback is that such a pressing device 21, which is to be tightly fitted around such a rod 14 and seam 15, may damage the bag. A yet further drawback is that, due to the relatively large size of such a seam, only one pair of seams can be applied, thus restricting the number of possible changes in operational volume of the bag. Also, due to the relatively large size of such a seam and its fixed position within the bag, the minimal operational liquid volume in the bag is restricted to about 300 milliliter when using a bag having a total volume in the order of magnitude of 20 liter.

Clearly, the present invention takes away all these drawbacks encountered with the alternative solution provided by WO2008/153401A1.

Specific embodiments of the invention are set forth in the appended dependent claims.

In a preferable embodiment, the apparatus according to the invention comprises shape adjusting means for changing at least the shape of said upwardly facing outer surface structure of said support structure in such manner that, as a result of the flexibility of said container wall structure and as a result of such flexible bottom wall parts contactingly lying against said upwardly facing outer surface structure of said support structure, the shape of said container bottom wall structure is modified. By means of these shape adjusting means the apparatus may easily be tailored to different respective characteristics of different-respective cultivation processes to be carried out. For example, in performing a first such cultivation process with a first container in the apparatus, a first shape of the first container's bottom wall structure might be more suitable, while in performing a different, second such cultivation process with a different, second container in the apparatus, a different, second shape of the second container's bottom wall structure may be more suitable. Also, the shape adjusting means allows for applying changes to a container's bottom wall structure during an ongoing cultivation process with a particular container. In the last mentioned case the liquid motion inducing movement takes place at least before and after the container's bottom wall structure has been changed by the shape adjusting means. Said shape adjusting means for changing at least the shape of said outer surface structure of said support structure may be of various types. It may for example include generally known structure including interconnected beams and/or other parts whose orientations are adjustable (automatically or manually) relative to one another. It may also for example include one or more elements that are fillable with a fluid (gas or liquid), and whose shapes are variable depending on the filling status of such an element.

In another preferable embodiment of the invention the support structure comprises connection structure arranged for connection with measuring means of the container, said measuring means being arranged for measuring characteristics related to cellular activity in said interior space of the container, wherein said connection structure is arranged for allowing transmittal of said measured characteristics from said measuring means to monitoring means for allowing monitoring of said characteristics, and wherein at least part of said connection structure and at least part of said measuring means are located in the gutter. Thus locating parts of the connection structure and the measuring means in the gutter makes said monitoring reliable at all times, since, even when a very small starting culture is being cultivated in a large working-culture container, the gutter is the place where the occurrence of too small liquid levels is most effectively prevented. Furthermore, since the moving liquid medium is continuously driven into the gutter under the influence of gravity, the measuring means are flushed properly at all times.

In a further preferable embodiment of the invention said support structure of the apparatus comprises at least one insert element, the at least one insert element being releasably mountable within said support structure and being arranged for providing, in its mounted condition, at least part of said elongate downwardly recessed portion which causes said gutter. Mounting such insert element(s) within the apparatus is very easy. In fact, the application of such insert element(s) does not require other, complex support structure of the apparatus. Hence, such insert elements can easily be used in an existing apparatus, without complex rebuilding of the apparatus. Furthermore, the application of such insert element(s) provides very high flexibility. In fact, a number of differently shaped insert elements can be kept in stock, so that the insert element(s), tailored to the characteristics of a specific cultivation process to be carried out, can be selected from the stock. Also, during an ongoing cultivation process with a particular container, one or more of the mounted insert elements can be removed from the support structure and/or one or more insert elements may be mounted to the support structure in addition to one or more already mounted insert element(s). Additionally or alternatively, such insert element may be fillable with a fluid (gas or liquid), the shape of such insert element being adjustable depending on its filling status. Hence, it is also clear that the insert element(s) may be used as at least part of the shape adjusting means mentioned above.

In further preferable embodiments of the invention said moving, of said at least part of the support structure together with the container resting thereon, comprises swiveling to and fro about a first substantially horizontal pivot axis in a swiveling range smaller than a maximum range between minus thirty degrees and plus thirty degrees relative to a zero degrees reference position of the container. It is noted that the abovementioned document U.S. Pat. No. 6,190,913B1 discloses an example of such a swiveling motion about a first substantially horizontal pivot axis. That is, in U.S. Pat. No. 6,190,913B1 the bag 4 is secured to a rocking platform 1 that is rocked to and fro about the horizontal axis 2. However, such a swiveling motion about a first substantially horizontal pivot axis encompasses various other possible types of swiveling motion, such as for example the more specific types known from WO2007/001173A2, in which during the swiveling motion about the first substantially horizontal pivot axis (indicated by reference sign 5, 5B or 55 in WO2007/001173A2), the first pivot axis follows a cyclical closed-loop path (indicated by reference sign 6, 6B or 56 in WO2007/001173A2).

Regarding the abovementioned expression 'zero degrees reference position' of the container, it is remarked that in said example of U.S. Pat. No. 6,190,913B1 said zero degrees reference position corresponds to a horizontal position of the rocking platform 1 in U.S. Pat. No. 6,190,913B1, while in the examples of WO2007/001173A2 said zero degrees reference position corresponds to a horizontal position of the platform 7, 7A, 7B or 57 in WO2007/001173A2. More in general, the expression 'zero degrees reference position' of the container, as used in the present document, corresponds to the position of the container in which the surface area of a vertical projection of the container onto a horizontal reference plane is maximal.

In a further preferable embodiment of the invention the longitudinal direction of said elongate downwardly recessed portion is substantially transverse to said first pivot axis, so that the gutter has a longitudinal gutter direction also being substantially transverse to said first pivot axis. In another further preferable embodiment of the invention the longitudinal direction of said elongate downwardly recessed portion is substantially parallel to said first pivot axis, so that the gutter has a longitudinal gutter direction also being substantially parallel to said first pivot axis. The effects of applying a longitudinal gutter direction either being substantially transverse or being substantially parallel to said first pivot axis, may relate to various aspects, such as for example additional improvement of mixing behaviour and/or additional improving the degree of preventing damaging shear stress levels and/or additional improvements regarding the design and/or design freedom of the apparatus and/or container, etcetera. The additional improvements regarding such aspects will depend on various factors, such as for example dimensions and shapes of the container and/or dimensions and shapes of the gutter and/or types and characteristics of the swiveling motion and/or characteristics of the cell culture, etcetera. For these reasons, it will in some cases be more opportune to choose for a longitudinal gutter direction being substantially transverse to said first pivot axis, while in other cases it will be more opportune to choose for a longitudinal gutter direction being substantially parallel to said first pivot axis.

In some cases of performing a method according to the invention it may be opportune to initially swivel with mutually parallel pivot axis and longitudinal gutter direction, and to thereafter change to swivel with mutually transverse pivot axis and longitudinal gutter direction, or vice versa. For example, in case of an extremely small starting culture being cultivated in a very large working-culture container, initially swiveling with mutually parallel pivot axis and longitudinal gutter direction may be advantageous in view of creating liquid motion being evenly distributed over the longitudinal gutter direction, thus promoting an even distribution of the liquid layer thickness over the longitudinal gutter direction. And when the culture is expanding in the working-culture container it may at some point be advantageous to change the swiveling to swiveling with mutually transverse pivot axis and longitudinal gutter direction. Such a change in the relative swiveling directions may be performed in various ways, for example by means of the abovementioned shape adjusting means and/or for example by rearranging the abovementioned insert elements, or replacing them by other insert elements, such that the longitudinal gutter direction is changed relative to the pivot axis.

Another way of realizing such a change in the relative swiveling direction may be to make use of two different substantially horizontal pivot axes, i.e. two pivot axes being mutually transverse. This has the advantage that it is easy to change from swiveling about the first pivot axis to swiveling about the second pivot axis, or vice versa, which takes away the need to use the abovementioned shape adjusting means and/or to rearrange or replace the abovementioned insert elements for carrying out the change in the relative swiveling direction.

Therefore, in a further preferable embodiment of the invention, the longitudinal direction of said elongate downwardly recessed portion is substantially transverse to said first pivot axis, while at the same time it is substantially parallel to a second substantially horizontal pivot axis, wherein said moving, by said movement mechanism of said at least part of the support structure together with the container resting thereon further comprises swiveling to and fro about said second pivot axis in a swiveling range smaller than a maximum range between minus thirty degrees and plus thirty degrees relative to a zero degrees reference position of the container.

These and other aspects of the invention will be apparent from and elucidated with reference to the embodiments described hereinafter by way of non-limiting examples only and with reference to the schematic figures in the enclosed drawing.

Figure 2:
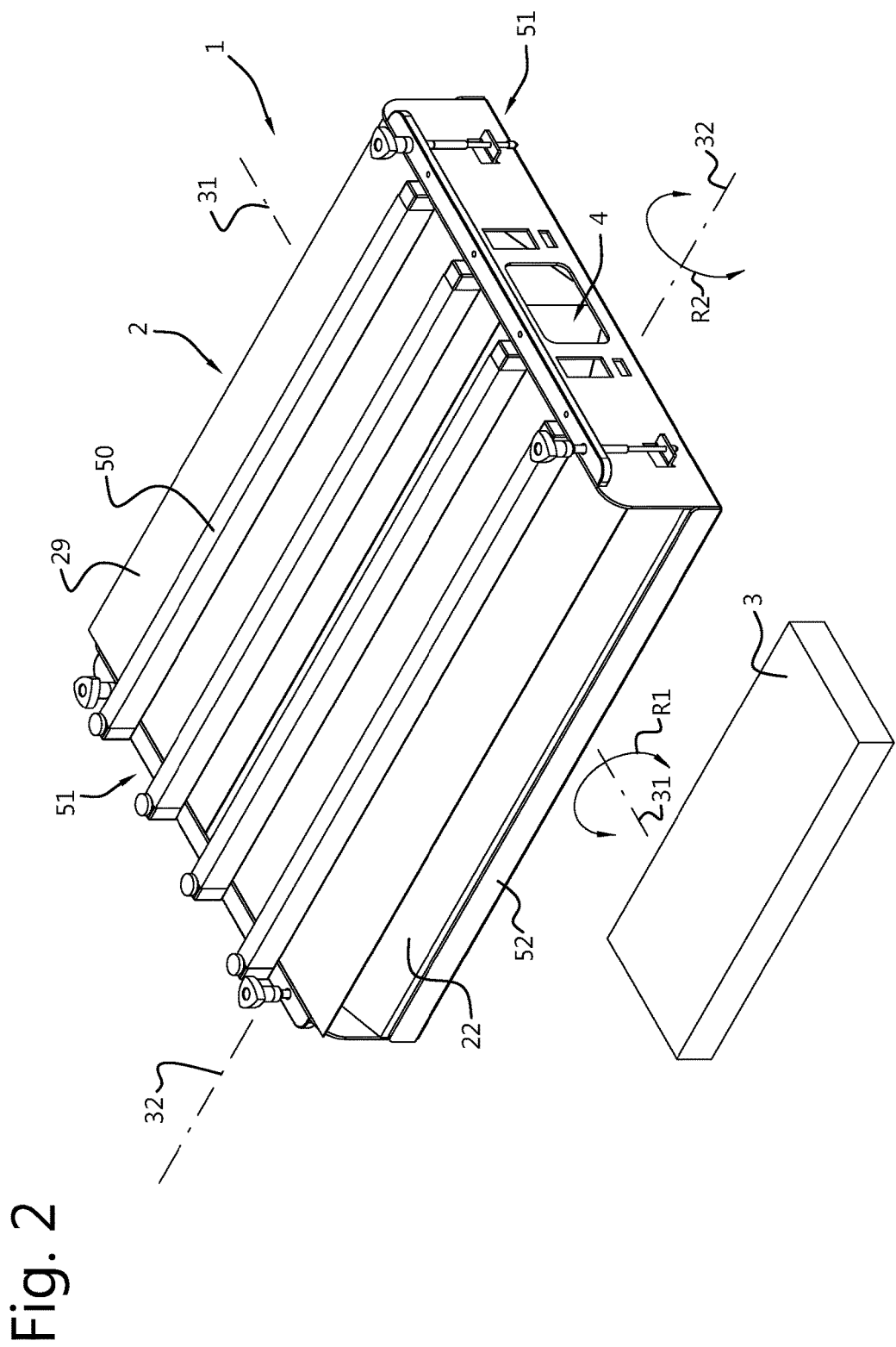
FIG. 2 shows, in a perspective view, an example of an embodiment of an apparatus according to the invention, wherein the container of FIG. 1 has been placed in the apparatus.
Figure 3:
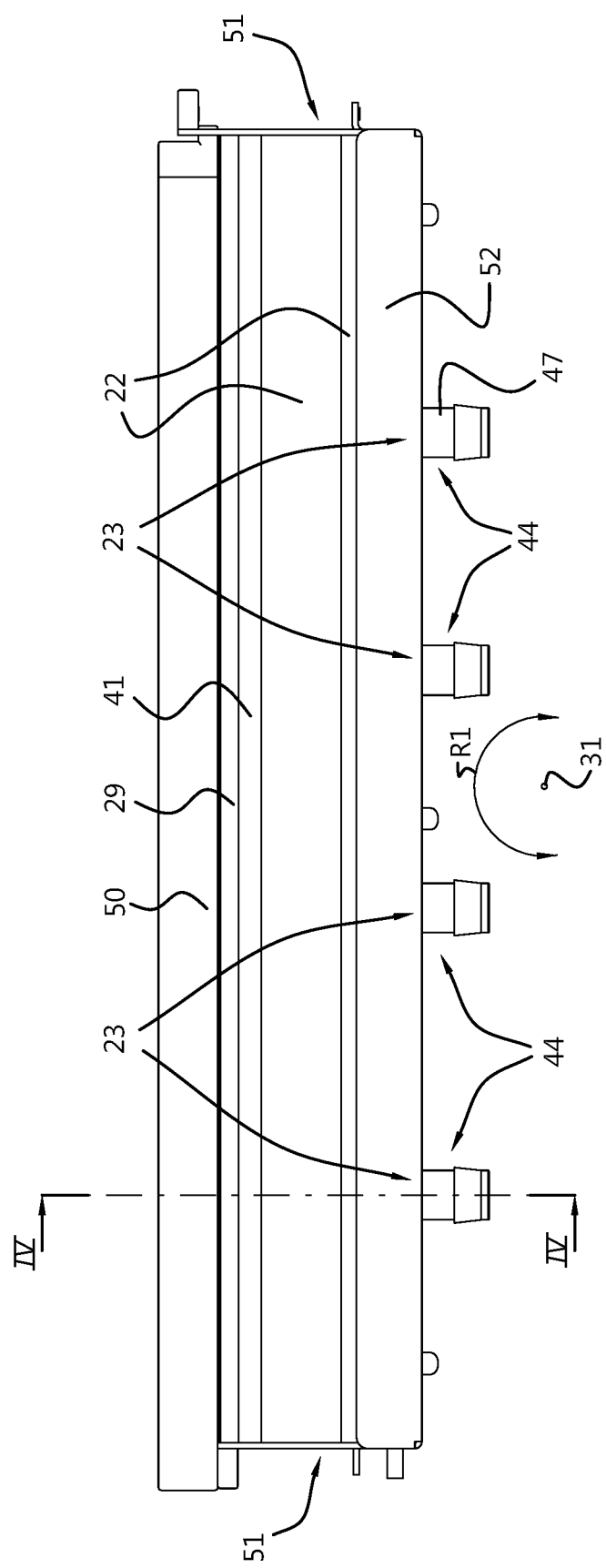
FIG. 3 shows part of the apparatus of FIG. 2 in side view.
Figure 4:
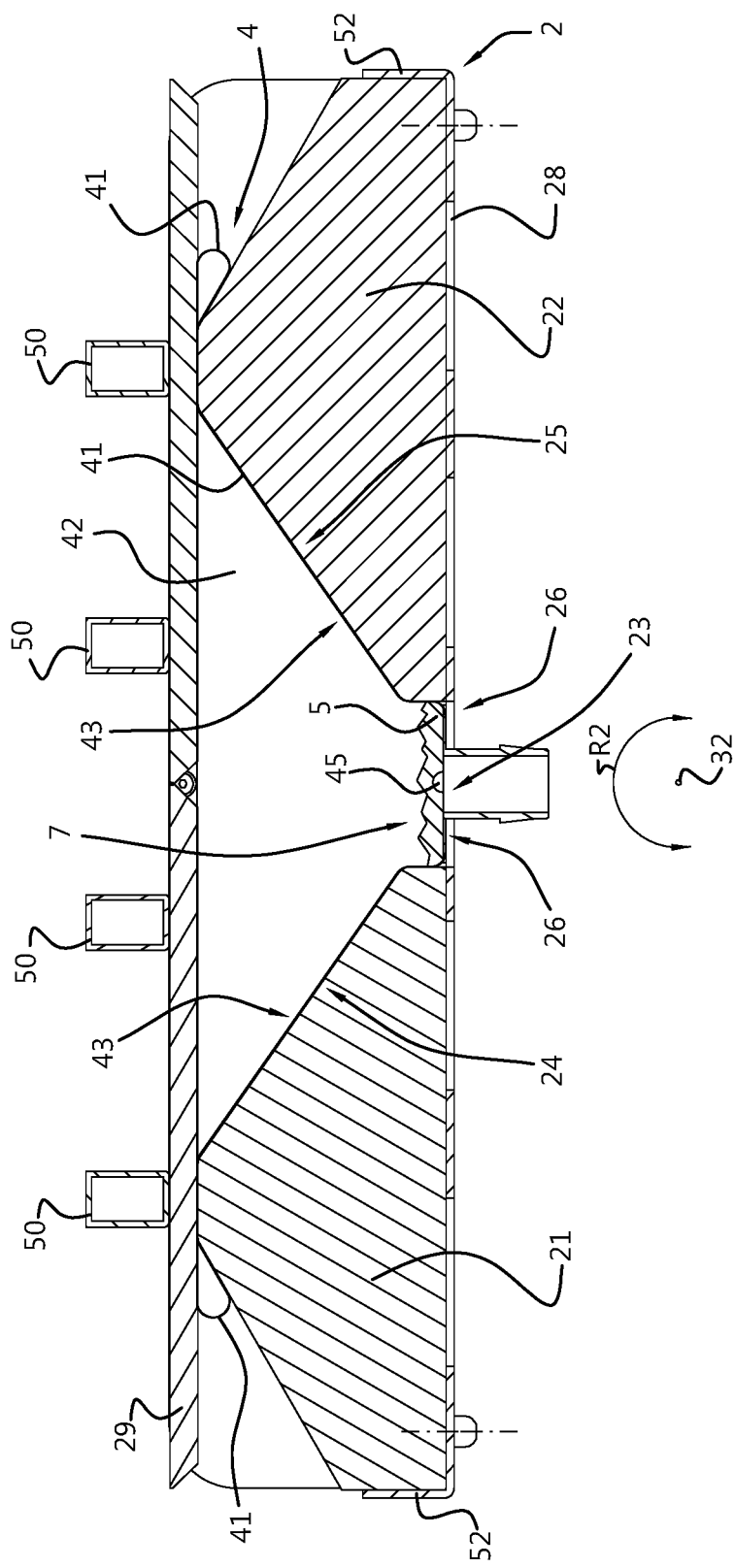
FIG. 4 shows part of the apparatus of FIG. 2 in a cross-section taken along the broken line indicated in FIG. 3 together with corresponding viewing direction IV.

The container shown in these figures is indicated by reference numeral 4. The apparatus shown in FIG. 2 is indicated by reference numeral 1. Furthermore, FIGS. 2-4 show two horizontal and mutually orthogonal pivot axes 31 and 32. Also, FIG. 2 shows, in a highly schematical way, the movement mechanism 3 of the apparatus 1.

Figure 1:
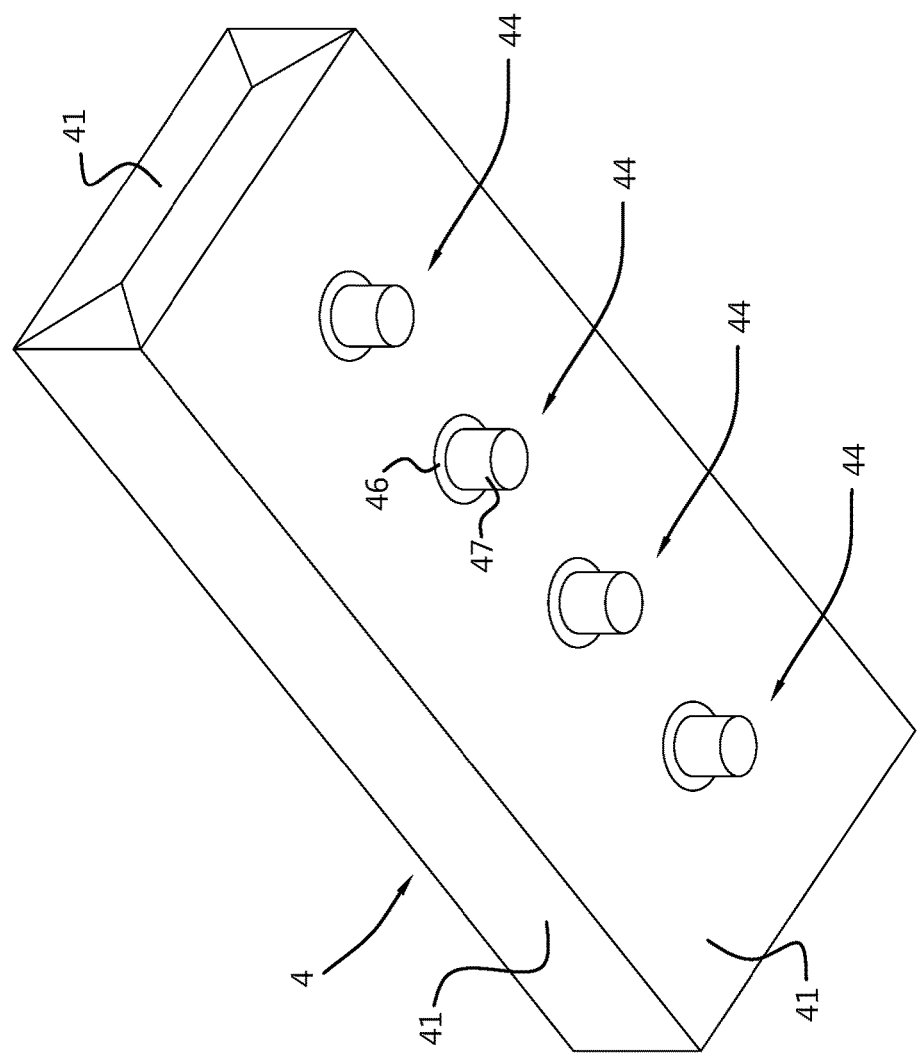
FIG. 1 shows, in a perspective view, an example of an embodiment of a container for use in a method and in an apparatus according to the invention.

In the shown example, the container 4 may assume the shape of a substantially rectangular box formed by flexible walls 41 when the container 4 is filled to a certain extent with one or more fluid(s), see FIG. 1. When placed in the apparatus 1, see FIGS. 2-4, the container 4 assumes a form which differs from said rectangular box form. The different form is possible thanks to the flexibility of the walls 41. The interior space of the container 4 is indicated by reference numeral 42, see FIG. 4.

In the shown example, the container 4 comprises a number of measuring elements 44 being arranged for measuring characteristics related to cellular activity in the interior space 42 of the container 4 for allowing monitoring of said characteristics. Similar such measuring elements are for example known from WO2008/153401A1. In the shown example, each measuring element 44 comprises a circumferential wall 47 having a circumferential flange 46 being sealingly connected to the one of the walls 41 that forms a bottom of the container 4, as shown in FIG. 1. Each measuring element 44 may for example comprise a sensor element 45 (see FIG. 4), similar to measuring elements known from for example WO2008/153401A1.

Furthermore, the container 4 may comprise various additional accessories, such as for example connection elements for supplying fluids to and/or for removing fluids from the interior space 42, as required. For simplicity, such additional accessories have been omitted in the figures.

It is noted that, instead of the shown example, various other shapes of containers for use in a method and apparatus according to the invention are possible. Materials of walls and accessories of the container, such as the measuring elements and other connection elements, are known in the art.

The support structure of the apparatus 1 is indicated by reference numeral 2. In the shown example, the support structure 2 comprises a rectangular platform 28 with two upstanding walls 52 at two opposing edges thereof (best seen in FIG. 4). At two other opposing edges, the platform 28 has two further upstanding wall structures 51 (see FIGS. 2 and 3). The support structure 2 further comprises a topping structure in the form of a top plate 29 with reinforcing bars 50 on top of it, the top plate 29 being fixedly connected to the wall structures 51. It is remarked that the reinforcing bars 50 have been provided to the top plate 29 in view of withstanding possible high overpressures in the container 4 relative to the direct outside environment of the container.

In the shown example, the support structure 2 further comprises two insert elements 21 and 22 (best seen in FIG. 4), being releasably mounted within the support structure 2. The two insert elements 21 and 22 are located between the platform 28 and the top plate 29, between the two opposing upstanding walls 52, and between the two opposing upstanding wall structures 51. In the example, each of the two insert elements 21 and 22 is extending over the full length from one to the other of the two opposing upstanding wall structures 51, i.e. in the direction of the pivot axis 32. Over its entire length in the direction of that pivot axis 32, each of the two insert elements 21 and 22 has constant cross-sectional shape, i.e. the cross-sectional shape shown in FIG. 4.

As mentioned, in FIGS. 2-4 the container 4 has been placed in the apparatus 1. The placed container 4 is best seen in FIG. 4, in which reference numeral 43 indicates the container bottom wall structure, defined as the part of the container wall structure 41 at the downwards facing side of the container 4 and forming a bottom of the container 4. FIG. 4 shows that flexible bottom wall parts of the container bottom wall structure 43 are contactingly lying against an upwardly facing outer surface structure of the support structure 2. In the shown example, this upwardly facing outer surface structure comprises a part 26 of the outer upper surface of the platform 28, as well as the inclined outer surfaces 24 and 25 of the insert elements 21 and 22, respectively. In fact, said part 26 together with said inclined outer surfaces 24 and 25 are forming an elongate downwardly recessed portion of the upwardly facing outer surface structure of the support structure 2. This elongate downwardly recessed portion 24, 25, 26 causes a gutter 7 in the container bottom wall structure 43. In FIG. 4, reference numeral 5 indicates a relatively small amount of liquid medium in the container 4.

Reference numerals 23, indicated in FIGS. 3 and 4, denote circular passageways through the platform 28. Each measuring element 44 is extending with its circumferential wall 47 through such a passageway 23. To each measuring element 44 there may for example be connected a line comprising an optical fiber, for example by plugging such an optical fiber line onto the circumferential wall 47, in such manner that the optical fiber line may transmit measured characteristics from the sensor 45 to monitoring means for allowing monitoring of said characteristics.

As mentioned, the apparatus 1 comprises a movement mechanism 3 (shown only very schematically in FIG. 2). In the shown example, the movement mechanism 3 is arranged for moving the support structure 2 together with the container 4 thus resting thereon, to thereby induce motion to the liquid medium 5 in the container, which motion contributes to cell growth.

In the shown example, the first horizontal pivot axis 31 is substantially transverse to the longitudinal gutter direction of the gutter 7, and the second horizontal pivot axis 32 is substantially parallel to the longitudinal gutter direction of the gutter 7.

The moving, by the movement mechanism 3 of at least part of the support structure 2 together with the container 4 resting thereon may comprise swiveling to and fro about the first horizontal pivot axis 31, as indicated by the double arrow 'R1' in FIGS. 2 and 3. Said moving may also comprise swiveling to and fro about the second horizontal pivot axis 32, as indicated by double arrow 'R2' in FIGS. 2 and 4. These swiveling motions R1 and R2 may each be performed in a swiveling range smaller than a maximum range between minus thirty degrees and plus thirty degrees relative to the zero degrees reference position of the container. In the shown example, said zero degrees reference position of the container corresponds to the situation in which the platform 28 is in its horizontal position, as shown.

In the foregoing specification, the invention has been described with reference to specific examples of embodiments of the invention. It will, however, be evident that various modifications and changes may be made therein without departing from the broader scope of the invention as set forth in the appended claims.

For instance, in the shown example, the elongate downwardly recessed portion of the upwardly facing outer surface structure is partly formed by the surfaces 24 and 25 having mutually opposite straight (linear) inclinations (see FIG. 4) for causing the gutter 7 in the container's bottom wall structure. However, according to the invention, various alternatives for the elongate downwardly recessed portion of the upwardly facing outer surface structure are possible for causing a gutter in the container's bottom wall structure, for example by applying non-linear inclinations, such as curved inclinations (e.g. hyperbolic, parabolic, etcetera), or piece-wise combinations of linear inclinations having different inclination angles, or piece-wise combinations of linear and curved inclinations, etcetera.

Also it is remarked that the invention is not limited to the presence of one or more measuring elements, such as the shown measuring elements 44, at a bottom wall of the container. When, for example, the measuring elements 44 would be absent in the shown example, the inclined surfaces 24 and 25 may for example connect to one another at their lower edges to form (as seen in a cross section analogous to the cross section of FIG. 4) a V-shaped recessed portion of the upwardly facing outer surface structure of the support structure, hence a recessed portion without the part 26 of the outer upper surface of the platform 28.

However, other modifications, variations and alternatives are also possible. The specifications and drawings are, accordingly, to be regarded in an illustrative rather than in a restrictive sense.

The invention claimed is:

1. A method for cultivating cells, comprising the steps of:
providing a container comprising an at least partly flexible container wall structure defining an interior space of the container;
placing the container in an apparatus such that the container thereby is at least resting on a support structure of the apparatus, wherein, when the container is thus resting, a container bottom wall structure is defined as the part of the container wall structure at the downwards facing side of the container and forming a bottom of the container, and wherein at least flexible bottom wall parts of said container bottom wall structure are contactingly lying against an upwardly facing outer surface structure of said support structure;
introducing a gas, a liquid medium and a cell culture into said interior space;
operating said apparatus such that at least part of said support structure together with the container thus resting thereon are moving, thereby inducing a motion to the liquid medium in the container, which motion contributes to cell growth of the cell culture;
characterized in that,
at least temporarily during said moving, said upwardly facing outer surface structure of said support structure of the apparatus comprises an elongate downwardly recessed portion which causes, also as a result of the flexibility of said bottom wall parts and also as a result of said flexible bottom wall parts contactingly lying against said upwardly facing outer surface structure of said support structure, a gutter in said container bottom wall structure;
wherein said moving, of said at least part of the support structure together with the container resting thereon, comprises swiveling to and fro about a first substantially horizontal pivot axis in a swiveling range smaller than a maximum range between minus thirty degrees and plus thirty degrees relative to a zero degrees reference position of the container and
wherein the gutter has a longitudinal gutter direction being substantially transverse to said first pivot axis.

2. The method according to claim 1, further comprising the step of changing at least the shape of said upwardly facing outer surface structure of said support structure in such manner that, as a result of the flexibility of said container wall structure and as a result of such flexible bottom wall parts contactingly lying against said upwardly facing outer surface structure of said support structure, the shape of said container bottom wall structure is modified, said moving taking place at least before and after said step of changing at least said outer surface structure.

3. The method according to claim 1, wherein the support structure comprises connection structure arranged for connection with measuring means of the container, said measuring means being arranged for measuring characteristics related to cellular activity in said interior space of the container, wherein said connection structure is arranged for allowing transmittal of said measured characteristics from said measuring means to monitoring means for allowing monitoring of said characteristics, and wherein at least part of said connection structure and at least part of said measuring means are located in the gutter.

4. The method according to claim 1, wherein said support structure of the apparatus comprises at least one insert element, the at least one insert element being releasably mounted within said support structure and providing at least part of said elongate downwardly recessed portion which causes said gutter.

\* \* \* \* \*